United States Patent
Ford et al.

(10) Patent No.: US 9,732,100 B2
(45) Date of Patent: Aug. 15, 2017

(54) PREPARATION OF ALKALINE EARTH METAL-COMPLEXED METAL BISAMIDES FROM METAL MONOAMIDES

(71) Applicant: BAYER CROPSCIENCE AKTIENGESELLSCHAFT, Monheim (DE)

(72) Inventors: Mark James Ford, Schmitten (DE); Marc Mosrin, Frankfurt am Main (DE)

(73) Assignee: BAYER CROPSCIENCE AG, Monheim (DE)

(*) Notice: Subject to any disclaimer, the term of this patent is extended or adjusted under 35 U.S.C. 154(b) by 0 days.

(21) Appl. No.: 14/766,160

(22) PCT Filed: Feb. 11, 2014

(86) PCT No.: PCT/EP2014/052588
§ 371 (c)(1),
(2) Date: Aug. 6, 2015

(87) PCT Pub. No.: WO2014/124915
PCT Pub. Date: Aug. 21, 2014

(65) Prior Publication Data
US 2015/0368277 A1    Dec. 24, 2015

(30) Foreign Application Priority Data
Feb. 12, 2013  (EP) .................................... 13154935

(51) Int. Cl.
*C07D 239/30* (2006.01)
*C07F 3/06* (2006.01)
*C07F 3/02* (2006.01)

(52) U.S. Cl.
CPC .............. *C07F 3/06* (2013.01); *C07D 239/30* (2013.01); *C07F 3/02* (2013.01)

(58) Field of Classification Search
CPC ............ C07F 3/06; C07F 3/02; C07D 239/30
See application file for complete search history.

(56) References Cited

U.S. PATENT DOCUMENTS 9,079,925 B2    7/2015  Ford et al.

FOREIGN PATENT DOCUMENTS

| WO | 2008138946 A1 | 11/2008 |
|---|---|---|
| WO | 2010092096 A1 | 8/2010 |
| WO | 2013120878 A1 | 8/2013 |

OTHER PUBLICATIONS

Mosrin, Org Letters, vol. 11(15), 3406-3409, 2009.*
Mosrin, CA 150:191453, abstract only of Synthesis, vol. 22, 3697-3702, 2008.*
Mosrin, Org Letters, vol. 10(12), 2497-2500, 2008.*
Rohbogner, 2010, TMP2Mg*2LiCl and Related bases for the Metalation of Unsaturated substrates and the Roll of the Phosphorodiamidate Directing Group, 1-177.*
International Search Report from PCT/EP2014/052588, mailed May 14, 2014.
Wunderlich et al., "Efficient Preparation of Polyfunctional Organometallics via Directed Ortho-Metallation", Practical Synthetic Procedures, No. 15, 2010, pp. 2670-2678, XP002699126.
Wunderlich et al., "(tmp)2Zn·2 MgCl2·2 LiCl: A Chemoselective Base for the Directed Zincation of Sensitive Arenes and Heteroarenes", Synthetic Methods, Wiley-VCH Verlag GmbH & Co. KGaA, Weinheim, Angew. Chem. Int. Ed., 2007, 46, pp. 7685-7688.
Mosrin, et al., "TMPZnCl·LiCl: A New Active Selective Base for the Directed Zincation of Sensitive Aromatics and Heteroaromatics", Organic Letters, 2009, vol. 11, No. 8, Department Chemie & Biochemie, Munchen, Germany, pp. 1837-1840.

* cited by examiner

*Primary Examiner* — D M Seaman
(74) *Attorney, Agent, or Firm* — McBee Moore Woodward Vanik IP; Susan McBee; David Woodward

(57) ABSTRACT

The present invention relates to a process for preparing alkaline earth metal-complexed metal bisamides of the formula (I) from metal monoamides of the formula (II). The present invention further relates to a process for preparing alkaline earth metal monoamides of the formula (II-AE), to novel LiCl-free alkaline earth metal monoamides of the formula (II-AE-L), and to the use of these alkaline earth metal monoamides for metallation of aromatics, heteroaromatics, alkenes, alkynes and other organic compounds having activated C—H bonds.

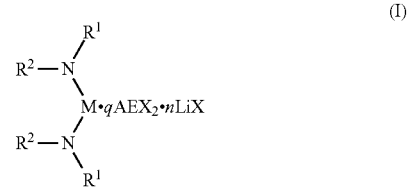

(I)

20 Claims, No Drawings

PREPARATION OF ALKALINE EARTH METAL-COMPLEXED METAL BISAMIDES FROM METAL MONOAMIDES

CROSS REFERENCE TO RELATED APPLICATIONS

This application is a §371 National Stage Application of PCT/EP2014/052588, filed 11 Feb. 2014, which claims priority to EP 13154935.4, filed 12 Feb. 2013.

BACKGROUND

Field of the Invention

The present invention relates to a process for preparing alkaline earth metal-complexed metal bisamides of the formula (I) from metal monoamides of the formula (II). The present invention further relates to a process for preparing alkaline earth metal monoamides of the formula (II-AE), to novel LiCl-free alkaline earth metal monoamides of the formula (II-AE-L), and to the use of these alkaline earth metal monoamides for metallation of aromatics, heteroaromatics, alkenes, alkynes and other organic compounds having activated C—H bonds.

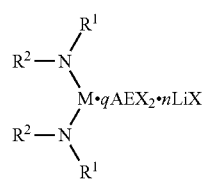

Description of Related Art

The preparation of aromatic and heteroaromatic molecules is of great significance because of the high biological potency thereof. Consequently, these structural elements are constituents of many active pharmaceutical and agrochemical ingredients. The direct metallation of aromatics, heteroaromatics or activated C—H bonds has become established as an excellent tool for functionalization of aromatics, heteroaromatics and other organic compounds.

For this purpose, predominantly lithium alkyls or lithium amides have been used to date as bases.

As an alternative, efficient bases have been developed for metallation, especially magnesiation and zincation, of aromatics and heteroaromatics. Zinc amide or magnesium amide bases, for example Mg-TMP and Zn-TMP (TMP=2,2,6,6-tetramethylpiperidyl), complexed with lithium chloride (LiCl), for example TMPMgCl.LiCl, TMPZnCl.LiCl, TMP$_2$Zn.2MgCl$_2$.2LiCl, are versatile metallation reagents, as described in WO 2010/092096 or WO 2008/138946. They have high kinetic basicity coupled with very good chemo- and regioselectivities. In addition, zinc amide bases, for example, can be stored under protective gas as solutions in THF (tetrahydrofuran) for weeks, without losing their activity.

For synthesis of the bases, typically amines, for example TMP, are lithiated with equimolar amounts of butyllithium (BuLi). Owing to the high cost of BuLi, zinc amide bases are too expensive for a multitude of industrial syntheses. There is therefore still an urgent need for an alternative, preferably less expensive and/or more favourable, route to metal amide bases, especially dispensing with the use of expensive BuLi.

SUMMARY

The present invention relates primarily to a process for preparing alkaline earth metal-complexed metal bisamides of the formula (I) or tautomers thereof

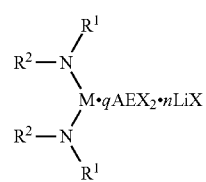

where

AE is an alkaline earth metal, preferably selected from calcium and magnesium;

M is a metal selected from metals from groups 3, 4, 7, 8, 9, 10, 11, 12, 13 of the Periodic Table of the Elements (PTE) and the group of the lanthanoids;

X is a halogen atom selected from the group consisting of fluorine, chlorine, bromine and iodine;

n is a number from 0 to 6;

q is a number from 1 to 6;

$R^1$ and $R^2$ are each independently selected from the group consisting of $(C_1-C_8)$alkyl optionally substituted by 1-2 $R^3$ radicals;

or $R^1$ and $R^2$ together form a —$(CH_2)_4$—, —$(CH_2)_5$—, or —$(CH_2)_2O(CH_2)_2$— group, where each of these groups may optionally be substituted by 1-4 $R^4$ radicals;

$R^4$ is independently selected from halogen, $(C_1-C_3)$alkyl, $(C_1-C_3)$alkoxy, $(C_1-C_3)$haloalkoxy, and $(C_2-C_4)$dialkylamino;

by reacting one or more metal monoamides of the formula (II)

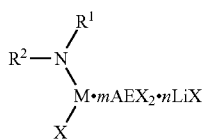

in which M, AE, X, n, q, $R^1$ and $R^2$ are each as defined above, and m=q−1, with one or more metallic alkaline earth metals (i.e. with one or more alkaline earth metals in elemental form), preferably with metallic magnesium and/or metallic calcium.

The reduction of the metal (M) by the elemental alkaline earth metal (AE), preferably by metallic magnesium and/or calcium, in the process according to the invention makes it possible to dispense with the use of costly BuLi.

DETAILED DESCRIPTION OF A PREFERRED EMBODIMENT

The process according to the invention is preferably effected by adding the metal monoamide(s) of the formula (II). For this purpose, preferably, the metallic alkaline earth metal (AE) or a mixture of metallic alkaline earth metals is initially charged, and the metal monoamide(s) of the formula (II) is/are added to the alkaline earth metal (mixture).

The AE-complexed metal bisamides of the formula (I) obtainable by the process according to the invention are especially suitable for metallation under mild conditions. They are therefore particularly suitable for conversion of sensitive (hetero)aromatics and are tolerated by sensitive functional groups, for example nitro, aldehyde or F, which is frequently not the case for the corresponding lithium or magnesium bases.

TMPZnCl.LiCl has been described in the literature as a mild base for the metallation of sensitive (hetero)aromatics at temperatures around 20° C. (see Org. Lett. 2009, 11(8), 1837-1840). For example, the reaction of 2-chloro-3-nitropyridine with $(TMP)_2Zn.2MgCl_2.2LiCl$ is also described in the literature (see Angew. Chem. Int. Ed. 2007, 46, 7685-7688). Synthesis 2010, 2670-2678 describes the preparation of functionalized organometallic compounds using metal amides such as $(TMP)_2Mn.2MgCl_2.4LiCl$ or $(TMP)_2Fe.2MgCl_2.4LiCl$.

The term "halogen" or "halogen atom" means, for example, fluorine, chlorine, bromine or iodine. When the term is used for a radical, "halogen" or "halogen atom" means, for example, a fluorine, chlorine, bromine or iodine atom.

Alkyl means a straight-chain, branched or cyclic hydrocarbyl radical. The expression "$(C_1-C_4)$alkyl", for example, is a brief notation for an alkyl radical having one to 4 carbon atoms in accordance with the standard range stated for carbon atoms and encompasses, for example, the methyl, ethyl, 1-propyl, 2-propyl, 1-butyl, 2-butyl, 2-methylpropyl, tert-butyl, cyclopropyl and cyclobutyl radicals. General alkyl radicals with a larger specified range of carbon atoms, e.g. "$(C_1-C_6)$alkyl", correspondingly also encompass straight-chain, branched or cyclic alkyl radicals with a greater number of carbon atoms, i.e. including the alkyl radicals having 5 and 6 carbon atoms.

Unless stated otherwise, for the hydrocarbyl radicals such as alkyl radicals, including in composite radicals, preference is given to the lower carbon skeletons, for example having 1 to 6 carbon atoms, or having 2 to 6 carbon atoms in the case of unsaturated groups. Alkyl radicals, including in the composite radicals such as alkoxy, haloalkyl etc., mean, for example, methyl, ethyl, cyclo-, n- or i-propyl, cyclo-, n-, i-, t- or 2-butyl, pentyls, hexyls such as cyclohexyl, n-hexyl, i-hexyl and 1,3-dimethylbutyl, heptyls such as cycloheptyl, n-heptyl, 1-methylhexyl and 1,4-dimethylpentyl.

Preferred cyclic alkyl radicals preferably have 3-8 ring carbon atoms, for example cyclopropyl, cyclobutyl, cyclopentyl or cyclohexyl. In the case of optionally substituted cyclic alkyl radicals, cyclic systems with substituents are included, also including substituents with a double bond on the cyclic alkyl radical, for example an alkylidene group such as methylidene.

In the case of optionally substituted cyclic alkyl radicals, polycyclic aliphatic systems are also included, such as bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl(norbornyl), adamantan-1-yl and adamantan-2-yl.

In the case of optionally substituted cyclic alkyl radicals, spirocyclic aliphatic systems are also included, for example spiro[2.2]pent-1-yl, spiro[2.3]hex-1-yl, spiro[2.3]hex-4-yl, 3-spiro[2.3]hex-5-yl.

Aryl is a mono-, bi- or polycyclic aromatic system having preferably 6 to 14, especially 6 to 10, ring carbon atoms, for example phenyl, indanyl, naphthyl, anthryl, phenanthrenyl and the like, preferably phenyl.

When two or more radicals form one or more rings, these may be carbocyclic, heterocyclic, saturated, partly saturated, unsaturated, for example also aromatic and optionally further substituted. The fused rings are preferably 5- or 6-membered rings, particular preference being given to benzofused cycles.

The substituents mentioned by way of example ("first substituent level") may, if they contain hydrocarboneous moieties, optionally be further substituted therein ("second substituent level"), for example by one of the substituents as defined for the first substituent level. Corresponding further substituent levels are possible. The term "substituted radical" preferably encompasses just one or two substituent levels.

Preferred substituents for the substituent levels are halogen, nitro, cyano, alkyl, dialkylamino, alkoxy, aryl, aryloxy, benzyl, benzyloxy, heterocyclyl and trialkylsilyl.

Preferred substituents composed of more than one substituent level are alkoxyalkyl such as monoalkoxyalkyl or dialkoxyalkyl, alkoxyalkoxy such as monoalkoxyalkoxy or dialkoxyalkoxy, benzyl, phenethyl, benzyloxy, haloalkyl, haloalkoxy, haloalkoxyalkyl and haloalkoxyalkyl.

In the case of radicals having carbon atoms, preference is given to those having 1 to 6 carbon atoms, preferably 1 to 4 carbon atoms, especially 1 or 2 carbon atoms. Preference is generally given to substituents from the group of halogen, preferably fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Substituted amino such as mono- or disubstituted amino is a radical from the group of the substituted amino radicals which are N-substituted, for example, by one or two identical or different radicals from the group of alkyl, alkoxy and aryl; preferably dialkylamino and diarylamino, such as optionally substituted N-alkyl-N-arylamino, and saturated N-heterocycles; preference is given to alkyl radicals having 1 to 4 carbon atoms; aryl is preferably phenyl or substituted phenyl.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, cyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, o-, m- and p-methoxyphenyl.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy$(C_1-C_4)$alkoxy, $(C_1-C_4)$alkoxy-$(C_1-C_4)$alkyl, $(C_1-C_4)$haloalkyl, $(C_1-C_4)$haloalkoxy, nitro and oxo, especially mono- or polysubstituted by radicals from the group of halogen, $(C_1-C_4)$alkyl, $(C_1-C_4)$alkoxy, $(C_1-C_4)$haloalkyl and oxo, and most preferably substituted by one or two $(C_1-C_4)$alkyl radicals.

Haloalkyl is alkyl fully substituted by identical or different halogen atoms, i.e. perhaloalkyls such as $CCl_3$, $CF_3$ or $CF_2CF_3$. Haloalkoxy is, for example, $OCF_3$.

Tautomers of the alkaline earth metal-complexed metal bisamides of the formula (I) are isomers which are interconverted rapidly by the migration of individual atoms or atom groups, meaning that several isomers interconvert rapidly and are in a chemical equilibrium with one another. Owing to this rapid conversion, the individual tautomers often cannot be isolated; the ratio of the tautomers in mutual equilibrium relative to one another is typically constant.

For the metal bisamides of the formula (I), for example, the tautomer equilibrium shown in Scheme 1 below can be postulated:

Scheme 1:

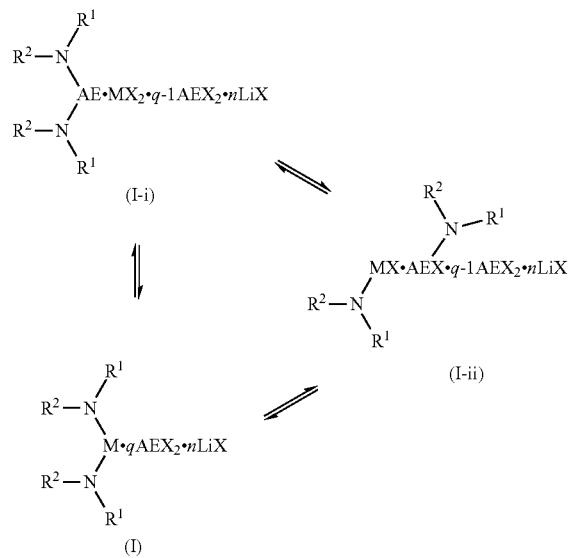

The formula (I) therefore also encompasses the tautomers (I-i) and (I-ii) in equilibrium therewith, and the oligomeric (preferably tetrameric) or polymeric complexes thereof, in which coordinating solvents are optionally also involved in the structures formed. The bond may be formed either via the halides X or via the nitrogen atoms.

A preferred embodiment of the invention relates to a process for preparing the calcium- or magnesium-complexed metal bisamides of the formula (I) and tautomers thereof, where
AE is calcium or magnesium;
M is a metal selected from Sc, Ti, Mn, Fe, Co, Ni, Cu, Zn and Al;
X is a halogen atom selected from chlorine and bromine;
n is a number from 0 to 6;
q is a number from 1 to 6;
$R^1$ and $R^2$ together form a —$(CH_2)_4$—, —$(CH_2)_5$— or —$(CH_2)_2O(CH_2)_2$— group, in which each of these groups may optionally be substituted by 1, 2, 3 or 4 $R^4$ radicals; where
$R^4$ is selected from methyl, ethyl, n-propyl and i-propyl.

A particularly preferred embodiment of the invention relates to a process for preparing the calcium- or magnesium-complexed metal bisamides of the formula (I) and tautomers thereof, where
AE is calcium or magnesium;
M is a metal selected from Ti, Mn, Fe, Zn and Al;
X is a halogen atom selected from chlorine and bromine;
n is a number from 0 to 4, preferably 0, 1, 2, 3 or 4;
q is a number from 1 to 3, preferably in turn 1, 2 or 3; $R^1$ and $R^2$ together form a —$(CH_2)_5$— group substituted by 4 methyl groups.

Most preferably, in a process according to the invention, the compounds of the formula (II) used are metal mono-2, 2,6,6-tetramethylpiperidides. In a particularly preferred process according to the invention, q=1.

In the process according to the invention, it is optionally additionally possible to use a haloamine of the formula (III) below, particular preference being given to the haloamine TMP-Cl,

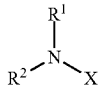

(III)

in which X, $R^1$ and $R^2$ are each as defined above, X, $R^1$ and $R^2$ preferably each having the definitions given above as preferred or particularly preferred.

The haloamines of the formula (III) typically used for preparation of the metal monoamides of the formula (II), for example the chloroamine TMP-Cl of the formula (III-1) used with particular preference in the context of the present invention, can be obtained by the methods described in the prior art; see, for example, Bodor et al., Jour. Pharm. Sci. 1974, 63, 1387; Kovacic et al., Chemical Reviews 1970, 70, 6, 639; Zakrzewski et al., Synthetic Communications 1988, 18(16&17), 2135; J. Org. Chem. 1997, 62, 16, 5631. Preference is given to effecting the synthesis by reacting the corresponding secondary amines with hypochlorites, as described in JACS, 1973, 6400 or by Toshimasa et al., Bull. Chem. Soc. Jap., 1972, 45, 1802 and Deno et al., JACS 1971, 93, 2065.

Metal monoamides of the formula (II) where M=Zn are commercially available, for example, as LiCl complexes (i.e. n≥1) and can be prepared in the presence of LiCl (WO 2010/092096). Alternatively, European patent application Nos. 12155980.1 (filed on 17 Feb. 2012) and 12171860.5 (filed on 13 Jun. 2012) and the patent application WO 2013/120878 based thereon describe a preparation process for metal monoamides without LiCl and without BuLi.

If the metal monoamides (II) are free of $AEX_2$, the process according to the invention affords a product of the formula (I) where only 1 molar equivalent (eq.) of $AEX_2$ is present, i.e. correspondingly q=1. This is especially advantageous with regard to the salt burden (salt load) of the synthesis mixture comprising the metal bisamide of the formula (I), since this salt burden, after appropriate workup of the reaction mixture, would get into the wastewater. Especially on the industrial or large industrial scale, this is a considerable advantage compared to the otherwise customary preparation of such metal bisamides, since typically at least 2 eq. of TMP-MgCl.LiCl have to be expected therein, and consequently a metal bisamide inevitably containing at least 2 eq. of $MgCl_2$ is formed.

The process according to the invention is performed preferably within a temperature range from +35 to −20° C., preferably at a temperature in the range from +25 to −10° C.

The reaction is preferably performed under protective gas atmosphere (preferably comprising or consisting of nitrogen and/or argon), in an aprotic, anhydrous diluent, preferably comprising one or more solvents selected from the group consisting of ethers and/or aromatics. Particular preference is given to using diluents comprising or consisting of coordinating solvents.

Preferred coordinating solvents are selected from THF, 2-methyltetrahydrofuran, tert-butyl methyl ether, 1,2-dimethoxyethane, diethyl ether, dibutyl ethers (preferably di-n-butyl ether) and/or cyclopentyl methyl ether.

In a preferred configuration, in addition to one or more ethers, preferably selected from the aforementioned ethers, one or more noncoordinating solvents are additionally used, preferably from the group consisting of aromatics, alkyl-substituted aromatics, alkanes, cycloalkanes and alkyl-substituted cycloalkanes. The noncoordinating solvent(s) is/are preferably selected from the group consisting of benzene, toluene, xylene, ethylbenzene, butylbenzene, n-hexane, n-heptane, isooctane, cyclohexane and methylcyclohexane.

The dilution of the reaction mixture is preferably adjusted such that the resulting solution of the AE-complexed metal bisamide can be used in subsequent reactions without further concentration. In this case, excess calcium or magnesium residues, calcium or magnesium halide, metal (M) or the corresponding metal halide $M^{n+}X^-_k$ are removed by filtration or decanting. It will be appreciated here that the index k in any metal halide ($M^{n+}X^-_k$) used in the process according to the invention is an integer corresponding to the valency of the metal ion of the metal (M). Preferably, k=2, 3 or 4, especially preferably k=2.

Based on the monoamide of the formula (II), in the process according to the invention, a total of at least 0.5 eq. of metallic alkaline earth metals (AE) is used, in order to achieve a maximum yield of metal bisamides of the formula (I).

Based on one eq. of monoamide of the formula (II), in the process according to the invention, preference is given to using a total of 0.5+W eq. of metallic alkaline earth metals (AE), where W is any number from 0 to 1.5, W preferably being any number from 0 to 1, further preferably any number from 0.05 to 0.75, more preferably any number from 0.1 to 0.6.

Accordingly, in the process according to the invention, preferably 0.5 to 2 eq. of metallic alkaline earth metals (AE) are used pro eq. of monoamide of the formula (II), more preferably 0.5 to 1.5 eq., further preferably 0.55 to 1.25 eq. and especially preferably 0.6 to 1.1 equivalents.

The total amount of haloamine of the formula (III) used in a process according to the invention is preferably 1.5W to 2.5W eq., preferably 1.75W to 2.25W eq., more preferably 1.9W to 2.1W eq., meaning that the amount of haloamine of the formula (III) is preferably matched to the amount of 0.5+W eq. of metallic alkaline earth metals (AE).

In a preferred configuration, the process according to the invention is performed by reacting 0.5 eq. of metallic alkaline earth metals (AE) (preferably calcium or magnesium) with one eq. of monoamide of the formula (II). In such a case, it is preferable in accordance with the invention when haloamine of the formula (III) is not additionally used.

In one configuration of the process according to the invention, more than 0.5 eq. of metallic alkaline earth metals is reacted with one eq. of monoamide of the formula (II), and the precipitated elemental metal (M) (for example Zn(0)) is preferably then removed from the reaction mixture, i.e. removed from the rest of the reaction mixture, preferably by filtering or decanting.

The remarks which follow are intended to illustrate by way of example how the process according to the invention can preferably be configured when more than 0.5 eq. of metallic alkaline earth metals is reacted with one eq. of monoamide of the formula (II).

In a particularly preferred configuration of the process according to the invention, more than 0.5 eq. (i.e. 0.5+W eq. where W>0 and W has the above-specified (preferred) definition) of metallic alkaline earth metals is reacted with one eq. of monoamide of the formula (II), as a result of which elemental metal (M) (for example Zn(0)) is precipitated, and then haloamine of the formula (III) (preferably TMP-Cl) is added to the reaction mixture formed. The haloamine of the formula (III) and the precipitated elemental metal (M) again form monoamide of the formula (II), which can subsequently react further (see also Scheme 2B below).

If a total of 0.6 eq. of alkaline earth metal AE is used (i.e. W=0.1), preferably 0.1 to 0.3 eq. of haloamine of the formula (III) (preferably TMP-Cl) is accordingly used. If a total of 0.75 eq. of alkaline earth metal AE is used (i.e. W=0.25), preferably 0.4 to 0.6 eq. of haloamine of the formula (III) (preferably TMP-Cl) is accordingly used. If a total of 1.0 eq. of alkaline earth metal AE is used (i.e. W=0.5), preferably 0.9 to 1.1 eq. of haloamine of the formula (III) (preferably TMP-Cl) is accordingly used.

It is also possible to use greater excesses of haloamine of the formula (III) (preferably TMP-Cl), but the above-specified amounts are preferred in the context of the present invention.

The process according to the invention is to be illustrated by way of example by the examples of the preparation of $(TMP)_2Zn \cdot MgCl_2 \cdot 2LiCl$ (I-1) shown in Schemes 2A and 2B below. In both cases, the temporary presence of TMP—Mg—Cl can be assumed.

Scheme 2A:

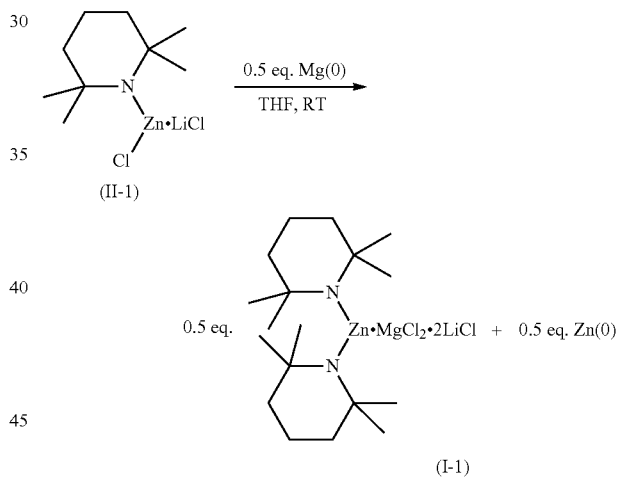

In the alternative shown in Scheme 2B, the metallic zinc (Zn(0)) obtained in the conversion of the elemental magnesium (Mg(0)) is first converted again by reaction with TMP-Cl (III-1) to TMP-ZnCl (II-1), which then reacts further in situ to give the metal bisamide (I-1).

Scheme 2B:

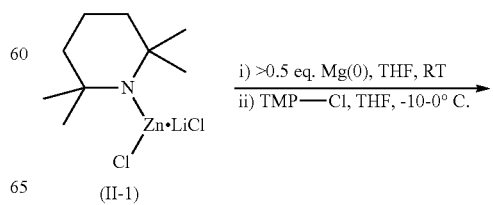

-continued

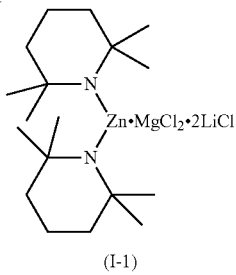

(I-1)

The elemental alkaline earth metal (AE) can also be used in the form of mixtures of calcium and magnesium. The combined use of magnesium and calcium makes it possible to obtain mixtures of the compounds of the formula (I) which, owing to synergies, may have advantages, for example an elevated solubility.

The metallic magnesium, Mg(0), can be used in the reaction in the form of turnings, beads or powder. Owing to the high active surface area, magnesium powder is preferred. Metallic calcium, Ca(0), is typically used in the reaction in the form of calcium powder.

For further activation of the metallic magnesium or calcium, it is optionally possible to add an activating reagent, e.g. i-Bu$_2$AlH (DibalH), dibromoethane or iodine, alone or in combination.

The metals (M) used in the context of the present invention are selected from metals of groups 3, 4, 7, 8, 9, 10, 11, 12, 13 of the Periodic Table of the Elements (IUPAC nomenclature) or the halides thereof, preferably chlorides, and the group of the lanthanoids or the halides thereof, preferably chlorides; the metals (M) are preferably selected from Sc, Ti, Mn, Fe, Co, Ni, Cu, Zn and Al or the halides thereof, preferably chlorides; the metals (M) are more preferably selected from Ti, Mn, Fe, Zn and Al or the halides thereof, preferably chlorides thereof. In connection with the present invention, the metals (M) zinc and manganese are of outstanding significance.

Closely connected to the above-described primary aspect of the present invention is a further aspect of the present invention. In the course of performance of the above-described process according to the invention for preparing the compounds of the formula (I) from compounds of the formula (II), it is possible to obtain compounds of the formulae (II-AE) and (II-AE-L) defined below.

In a further aspect, the present invention relates to a process for preparing an alkaline earth metal monoamide of the formula (II-AE), or the dimer, oligomer (preferably tetramer) or polymer thereof,

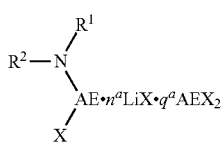

(II-AE)

where
AE is an alkaline earth metal;
$q^a$ is a number from 0 to 6;
$n^a$ is a number from 0 to 6;
X is a halogen atom selected from the group consisting of fluorine, chlorine, bromine and iodine;

$R^1$ and $R^2$ are each independently selected from the group consisting of $(C_1$-$C_8)$alkyl optionally substituted by 1-2 $R^3$ radicals,
or
$R^1$ and $R^2$ together form a —$(CH_2)_4$—, —$(CH_2)_5$—, or —$(CH_2)_2O(CH_2)_2$— group, where each of these groups may optionally be substituted by 1-4 $R^4$ radicals;
$R^3$ are each independently selected from halogen, $(C_1$-$C_3)$alkoxy, $(C_1$-$C_3)$haloalkoxy and $(C_2$-$C_4)$dialkylamino;
$R^4$ is selected from halogen, $(C_1$-$C_3)$alkyl, $(C_1$-$C_3)$alkoxy, $(C_1$-$C_3)$haloalkoxy and $(C_2$-$C_4)$dialkylamino or $(C_2$-$C_4)$alkoxycarbonyl,
by reacting one or more metal monoamides of the formula (II-M$^2$)

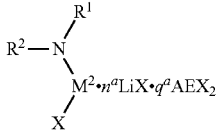

(II-M$^2$)

where
X, $q^a$, $n^a$, $R^1$ and $R^2$ are each as defined above (for (II-AE));
M$^2$ is a divalent metal selected from metals from groups 4, 7, 8, 9, 10, 11 and 12 of the PTE;
with a metallic alkaline earth metal, preferably with metallic magnesium or metallic calcium.

Unless explicitly stated otherwise below, the above remarks in connection with the preparation of the compounds of the formula (I) apply correspondingly to the process according to the invention for preparing the compounds of the formula (II-AE). This is especially true of the above embodiments in connection with AE, $R^1$, $R^2$, and X and of the above embodiments concerning the reaction conditions (especially also with regard to the diluent), and likewise of the respective configurations characterized as preferred and particularly preferred.

Preferably, the sum of $n^a+q^a>0$, i.e. is greater than zero; more preferably, the sum of $n^a+q^a>1$, i.e. greater than or equal to 1. In a preferred configuration $n^a=0$, i.e. an alkaline earth metal monoamide of the formula (II-AE) is preferably free of lithium halides LiX, especially free of LiCl.

In a preferred process for preparing an alkaline earth metal monoamide of the formula (II-AE), or the dimer, oligomer or polymer thereof, a total of 0.8 to 1.25 molar equivalents, preferably 0.9 to 1.1 molar equivalents, of metallic alkaline earth metal (AE) is used per molar equivalent of metal monoamide of the formula (II-M$^2$).

Preferably, the metals (M$^2$) are selected from Ti, Mn, Fe, Co, Ni, Cu and Zn, more preferably from Ti, Mn, Fe and Zn. In connection with the present invention, the metals (M$^2$) zinc and manganese are of outstanding significance.

A particularly preferred embodiment relates to a process according to the invention for preparing an alkaline earth metal monoamide of the formula (II-AE) where
AE is calcium or magnesium;
M$^2$ is a divalent metal selected from Ti, Mn, Fe, Cu, Ni and Zn;
X is chlorine;
$R^1$ and $R^2$ together form a —$(CH_2)_5$— group substituted by 4 methyl groups.

Preferably, the process according to the invention for preparing alkaline earth metal monoamide of the formula (II-AE) is performed in a diluent comprising one or more ethers or consisting of ethers, the ether(s) being selected from the group consisting of THF, 2-methyltetrahydrofuran, t-butyl methyl ether, 1,2-dimethoxyethane, diethyl ether, dibutyl ether and methyl cyclopentyl ether.

Preferably, the process according to the invention for preparing an alkaline earth metal monoamide of the formula (II-AE) is executed at a temperature in the range from +35 to −10° C.

A particularly preferred embodiment of the process according to the invention for preparation of an alkaline earth metal monoamide of the formula (II-AE) is characterized in that the elemental metal $M^2(0)$ formed in the reaction is removed, preferably by filtering or decanting.

In a further aspect, the present invention relates to particular alkaline earth metal monoamides of the formula (II-AE-L), or the dimers, oligomers or polymers thereof,

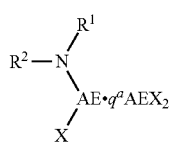

(II-AE-L)

where
AE is an alkaline earth metal, preferably magnesium or calcium;
$q^a$ is a number from 0 to 6;
X is a halogen atom selected from the group consisting of fluorine, chlorine, bromine and iodine;
$R^1$ and $R^2$ are each independently selected from the group consisting of $(C_1$-$C_8)$alkyl optionally substituted by 1-2 $R^3$ radicals,
or
$R^1$ and $R^2$ together form a —$(CH_2)_4$—, —$(CH_2)_5$—, or —$(CH_2)_2O(CH_2)_2$— group, where each of these groups may optionally be substituted by 1-4 $R^4$ radicals;
$R^3$ are each independently selected from halogen, $(C_1$-$C_3)$alkoxy, $(C_1$-$C_3)$haloalkoxy and $(C_2$-$C_4)$dialkylamino;
$R^4$ is selected from halogen, $(C_1$-$C_3)$alkyl, $(C_1$-$C_3)$alkoxy, $(C_1$-$C_3)$haloalkoxy and $(C_2$-$C_4)$dialkylamino and $(C_2$-$C_4)$ alkoxycarbonyl.

One of the advantages of the inventive metal monoamides over metal monoamides of similar structure known to date is that the inventive alkaline earth metal monoamides of the formula (II-AE-L) are free of lithium halides LiX, especially free of LiCl. The inventive alkaline earth metal monoamides of the formula (II-AE-L) are not only less expensive but also advantageous with regard to the comparatively lower salt burden (salt load).

The lower salt burden (salt load) of the mixture comprising the alkaline earth metal monoamide of the formula (II-AE-L), which, after workup of a corresponding reaction mixture, would get into the wastewater, is a considerable advantage, especially on the industrial or large industrial scale, over the otherwise customary alkali metal/alkaline earth metal monoamides comprising lithium halides LiX.

Unless explicitly stated otherwise below, the above remarks in connection with the compounds of the formula (I) apply correspondingly to the inventive compounds of the formula (II-AE-L). This is especially true of the above embodiments in connection with AE, $R^1$, $R^2$, and X, and likewise of the respective configurations characterized as preferred and particularly preferred.

Preferred alkaline earth metal monoamides of the formula (II-AE-L) are alkaline earth metal tetramethylpiperidides, especially alkaline earth metal 2,2,6,6-tetramethylpiperidides of the formula (II-AE-L-TMP)

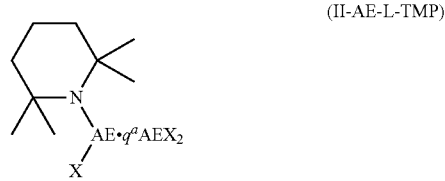

(II-AE-L-TMP)

In the formula (II-AE-L-TMP), preferably, AE=Mg and X=Cl.

In a preferred configuration, $q^a$=0, 1 or 2.
In a further preferred configuration, $q^a$=0.

The present invention further provides for the use of the alkaline earth-metal complexed metal bisamides of the formula (I), (I-i) or (I-ii) prepared in accordance with the invention, of the alkaline earth metal monoamides of the formula (II-AE) prepared in accordance with the invention, and of the inventive alkaline earth metal monoamides (II-AE-L)—as bases—for metallation of aromatics, heteroaromatics, alkenes, alkynes and other organic compounds having activated C—H bonds. The basicity, selectivity or activity thereof can be enhanced or influenced in an advantageous manner by the addition of lithium salts, for example lithium chloride, of crown ethers or of other coordinating reagents, either during the preparation or during the metallation of aromatics, heteroaromatics, alkenes, alkynes and other organic compounds having activated C—H bonds.

Organic compounds having activated C—H bonds are molecules having an increased tendency to release a hydrogen atom bonded to a carbon atom as protons, and hence, in a formal sense, to act as an acid. This is the case, for example, when the carbon atom is bonded to strongly electron-withdrawing groups such as carbonyls (in an ester, ketone or aldehyde), sulphones, nitriles, trifluoromethyl groups or nitro groups. For example, derivatives of malonic acid (pKa≈13) or acetylacetone (pKa≈9) have activated C—H bonds. C—C multiple bonds, as a result of the proximity of the carbon atoms, likewise ensure stronger polarization, such that α-alkenyl and -alkynyl groups, as, for example, in vinyl and propargyl groups, lead to CH activation. In addition, it is possible to deprotonate aromatic or heteroaromatic C—H bonds.

The present invention is to be illustrated in detail by the examples which follow.

Preparation of $(TMP)_2Zn \cdot MgCl_2 \cdot LiCl$

A dry, argon-filled Schlenk tube with a magnetic stirrer bar and septum is initially charged with magnesium powder (325 mesh-243 mg, 10 mmol) and iodine (15 mg, 0.06 mmol). After the addition of TMPZnCl.LiCl in THF (16.67 ml, 10 mmol), the reaction mixture was stirred at 25° C. for 24 h. 1-Chloro-2,2,6,6-tetramethylpiperidine (TMPCl; 1.93 g, 11 mmol) in anhydrous THF (15 ml) is then added dropwise with an infusion pump (rate: 15 ml/h) at −10° C. Thereafter, the reaction mixture is stirred at 25° C. for another 1 h and the brown solution is titrated with benzoic acid and N-phenyl-4-(phenylazo)aniline as an indicator. The concentration is 0.29 M (yield=91%).

Preparation of (TMP)$_2$Zn.CaCl$_2$.LiCl

A dry, argon-filled Schlenk tube with a magnetic stirrer bar and septum is initially charged with calcium powder (16 mesh-401 mg, 10 mmol) and iodine (15 mg, 0.06 mmol). After the addition of TMPZnCl.LiCl in THF (16.67 ml, 10 mmol), the reaction mixture was stirred at 25° C. for 24 h. 1-Chloro-2,2,6,6-tetramethylpiperidine (TMPCl; 1.93 g, 11 mmol) in anhydrous THF (15 ml) is then added dropwise with an infusion pump (rate: 15 ml/h) at −10° C. Thereafter, the reaction mixture is stirred at 25° C. for another 1 h and the brown solution is titrated with benzoic acid and N-phenyl-4-(phenylazo)aniline as an indicator. The concentration is 0.23 M (yield=76%).

Preparation of (TMP)$_2$Zn.MgCl$_2$.2LiCl

A dry, argon-filled Schlenk tube with a magnetic stirrer bar and septum is initially charged with magnesium powder (325 mesh-120 mg, 5 mmol) and iodine (15 mg, 0.06 mmol). After the addition of TMPZnCl.LiCl in THF (16.67 ml, 10 mmol), the reaction mixture was stirred at 25° C. for 24 h. The brown solution was decanted off from the precipitated solids and titrated with benzoic acid and N-phenyl-4-(phenylazo)aniline as an indicator. The concentration is 0.73 M (yield=93%).

Preparation of (TMP)$_2$Zn.CaCl$_2$.2LiCl

A dry, argon-filled Schlenk tube with a magnetic stirrer bar and septum is initially charged with calcium powder (16 mesh-200 mg, 5 mmol) and iodine (15 mg, 0.06 mmol). After the addition of TMPZnCl.LiCl in THF (16.67 ml, 10 mmol), the reaction mixture was stirred at 25° C. for 24 h. The brown solution was decanted off from the precipitated solids and then titrated with benzoic acid and N-phenyl-4-(phenylazo)aniline as an indicator. The concentration is 0.77 M (yield=98%).

Zincation of 2,4,6-trichloropyrimidine and Preparation of 5-iodo-2,4,6-trichloropyrimidine A dry, argon-filled Schlenk tube with a magnetic stirrer bar and septum is initially charged with 2,4,6-trichloropyrimidine (184 mg, 1 mmol) in anhydrous THF (1 ml). After addition of (TMP)$_2$Zn.MgCl$_2$.LiCl (1.2 mmol) in THF at 25° C., the mixture is stirred for another 1 h. Then a solution of iodine (355 mg, 1.4 mmol), dissolved in anhydrous THF (2 ml), is added dropwise and the reaction mixture is stirred at 25° C. for a further 1 h. After dilution with saturated aqueous NH$_4$Cl solution (30 ml) and extraction with ethyl acetate (3×30 ml), the combined organic phases are dried over Na$_2$SO$_4$. After distillative removal of the solvent and purification by column chromatography on silica gel (heptane:ethyl acetate), the desired compound (240 mg, 78%) is obtained as a colourless crystalline product.
$^{13}$C NMR (100 MHz, CDCl$_3$): δ=167.6, 159.3, 96.5 ppm.

Preparation of (TMP)MgCl.MgCl$_2$ from (TMP)ZnCl.MgCl$_2$

Preparation of (TMP)ZnCl.MgCl$_2$

In a dry, argon-filled Schlenk tube with a magnetic stirrer bar and septum, magnesium powder (325 mesh-1328 mg, 54.7 mmol) and zinc powder (3573 mg, 54.7 mmol) are initially charged and activated by addition of DIBAL-H (0.5 ml, 1 M in THF). After stirring for 5 min, the mixture is cooled to 0° C. and the stirring is stopped. After the addition of iodine (65 mg, 0.25 mmol), the mixture is stirred again and 1-chloro-2,2,6,6-tetramethylpiperidine (TMPCl; 2.4 g, 13.7 mmol) in anhydrous THF (15 ml) is added dropwise at 0° C. with an infusion pump (rate: 15 ml/h). Thereafter, the reaction mixture is stirred at 25° C. for another 30 min and the yellow solution is titrated with benzoic acid and N-phenyl-4-(phenylazo)aniline as an indicator. The concentration is 0.38 M (yield=96%).

Preparation of (TMP)MgCl.MgCl$_2$

A dry, argon-filled Schlenk tube with a magnetic stirrer bar and septum is initially charged with magnesium powder (325 mesh-243 mg, 10 mmol) and iodine (15 mg, 0.06 mmol). After the addition of (TMP)ZnCl.MgCl$_2$ (10 mmol), prepared as above, the reaction mixture is stirred at 25° C. for 24 h.

Preparation of (TMP)MgCl from (TMP)ZnCl

Preparation of (TMP)ZnCl

In a dry, argon-filled Schlenk tube with a magnetic stirrer bar and septum, zinc powder (3573 mg, 54.7 mmol) is initially charged and activated by addition of DIBAL-H (0.5 ml, 1 M in THF). After stirring for 5 min, the mixture is cooled to 0° C. and the stirring is stopped. After the addition of iodine (65 mg, 0.25 mmol), the mixture is stirred again and 1-chloro-2,2,6,6-tetramethylpiperidine (TMPCl; 2.4 g, 13.7 mmol) in anhydrous THF (15 ml) is added dropwise at 0° C. with an infusion pump (rate: 15 ml/h). Thereafter, the reaction mixture is stirred at 25° C. for another 30 min and the yellow solution is titrated with benzoic acid and N-phenyl-4-(phenylazo)aniline as an indicator. The concentration is 0.38 M (yield=96%).

Preparation of (TMP)MgCl

A dry, argon-filled Schlenk tube with a magnetic stirrer bar and septum is initially charged with magnesium powder (325 mesh-243 mg, 10 mmol) and iodine (15 mg, 0.06 mmol). After the addition of (TMP)ZnCl (10 mmol), prepared as above, the reaction mixture is stirred at 25° C. for 24 h.

The invention claimed is:
1. Process for preparing alkaline earth metal-complexed metal bisamide of formula (I) and/or a tautomer thereof

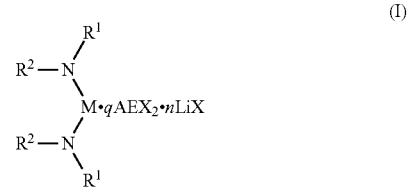

where
AE is one or more alkaline earth metals;
M is a metal selected from metals from groups 3, 4, 7, 8, 9, 10, 11, 12, 13 of the PTE and the group of the lanthanoids;
X is a halogen atom selected from the group consisting of fluorine, chlorine, bromine and iodine;
q is a number from 1 to 6;
n is a number from 0 to 6;

R¹ and R² together form a —(CH₂)₅— group substituted by 4 methyl groups;
by reacting one or more metal monoamides of formula (II)

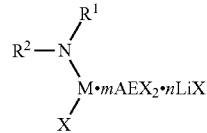
(II)

in which M, AE, X, q, n, R¹ and R² are each as defined above, and
m=q−1
with one or more metallic alkaline earth metals (AE).

2. Process according to claim 1, wherein a total of 0.5 to 2 molar equivalents of metallic alkaline earth metals (AE) is used per molar equivalent of metal monoamide of formula (II).

3. Process according to claim 1, wherein
AE is calcium and/or magnesium;
M is a metal selected from Ti, Mn, Fe, Zn and Al; and
X is chlorine.

4. Process according to claim 1, where
AE is calcium or magnesium;
M is Zn or Mn, and
X is chlorine.

5. Process according to claim 1, wherein the process is executed at a temperature in the range from +35 to −20° C.

6. Process according to claim 1, wherein the process is performed in a diluent comprising or consisting of one or more coordinating organic solvents.

7. Process according to claim 1, wherein the process is performed in a diluent comprising one or more ethers or consisting of ethers, the ether(s) being selected from the group consisting of THF, 2-methyltetrahydrofuran, t-butyl methyl ether, 1,2-dimethoxyethane, diethyl ether, dibutyl ether and methyl cyclopentyl ether.

8. Process according to claim 6, wherein the diluent additionally comprises one or more noncoordinating solvents selected from the group consisting of aromatics, alkyl-substituted aromatics, alkanes, cycloalkanes and alkyl-substituted cycloalkanes.

9. Process for preparing an alkaline earth metal monoamide of formula (II-AE), and/or the dimer, oligomer and/or polymer thereof,

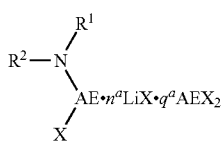
(II-AE)

where
AE is an alkaline earth metal;
$q^a$ is a number from 0 to 6;
$n^a$ is a number from 0 to 6;
X is a halogen atom selected from the group consisting of fluorine, chlorine, bromine and iodine;
R¹ and R² together form a —(CH₂)₅— group substituted by 4 methyl groups by reacting one or more metal monoamides of formula (II-M²)

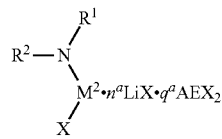
(II-M²)

where
X, $q^a$, $n^a$, R¹ and R² are each as defined above;
M² is a divalent metal selected from metals from groups 4, 7, 8, 9, 10, 11 and 12 of the PTE;
with a metallic alkaline earth metal.

10. Process according to claim 9, wherein a total of 0.8 to 1.25 molar equivalents of metallic alkaline earth metal (AE) is used per molar equivalent of metal monoamide of formula (II-M²).

11. Process according to claim 9, where
AE is calcium or magnesium;
M² is a divalent metal selected from Ti, Mn, Fe, Cu, Ni and Zn; and
X is chlorine.

12. Process according to claim 9, wherein the process is executed at a temperature in the range from +35 to −10° C.

13. Process according to claim 9, wherein the elemental metal M²(0) formed is removed.

14. Alkaline earth metal monoamide of formula (II-AE-L), and/or the dimer, oligomer and/or polymer thereof, free of lithium halides

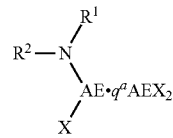
(II-AE-L)

where
AE is magnesium or calcium;
$q^a$ is a number from 0 to 6;
X is a halogen atom selected from the group consisting of fluorine, chlorine, bromine and iodine;
R¹ and R² together form a —(CH₂)₅— group substituted by 4 methyl groups.

15. A method for metallation of one or more aromatics, heteroaromatics, alkenes, alkynes and other organic compounds having activated C—H bonds comprising employing an alkaline earth metal monoamide of formula (II-AE) and/or the dimer, oligomer and/or polymer thereof, free of lithium halides,

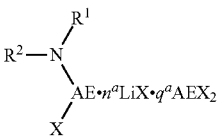
(II-AE)

wherein
AE is an alkaline earth metal;
$q^a$ is a number from 0 to 6;
$n^a$ is a number from 0 to 6;

X is a halogen atom selected from the group consisting of fluorine, chlorine, bromine and iodine;

$R^1$ and $R^2$ together form a —$(CH_2)_5$— group substituted by 4 methyl groups.

16. Process according to claim 6, wherein the diluent additionally comprises one or more noncoordinating solvents selected from the group consisting of benzene, toluene, xylene, ethylbenzene, butylbenzene, n-hexane, n-heptane, isooctane, cyclohexane and methylcyclohexane.

17. Process according to claim 1, wherein the reacting does not comprise the use of butyl lithium.

18. Process according to claim 9, wherein the reacting does not comprise the use of butyl lithium.

19. Process according to claim 1, wherein AE is metallic calcium.

20. Process according to claim 1, wherein AE is metallic magnesium.

\* \* \* \* \*